United States Patent [19]
Nolan

[11] Patent Number: 5,471,868
[45] Date of Patent: Dec. 5, 1995

[54] INSTRUMENT FOR MEASURING THE RELATIVE RESILIENCY OF GOLF GREENS

[76] Inventor: Donald E. Nolan, Youngs Rd., P.O. Box 64, Star Lake, N.Y. 13690

[21] Appl. No.: 338,239

[22] Filed: Nov. 14, 1994

[51] Int. Cl.⁶ .................. G01N 3/48; G01N 3/40
[52] U.S. Cl. .................................... 73/84; 73/81
[58] Field of Search ............................ 73/81, 84

[56] References Cited

U.S. PATENT DOCUMENTS

| | | | |
|---|---|---|---|
| 4,061,021 | 12/1977 | Baldwin et al. | 73/84 |
| 4,136,554 | 1/1979 | Larson | 73/81 |
| 4,302,967 | 12/1981 | Dufey | 73/84 |
| 4,887,459 | 12/1989 | Thomas | 73/81 |
| 5,291,774 | 3/1994 | Putnam, Jr. | 73/82 |

FOREIGN PATENT DOCUMENTS

| | | | |
|---|---|---|---|
| 1473354 | 5/1969 | Germany | 73/81 |
| 390414 | 11/1973 | U.S.S.R. | 73/84 |
| 586362 | 12/1977 | U.S.S.R. | 73/84 |
| 620871 | 8/1978 | U.S.S.R. | 73/84 |
| 1077977 | 3/1984 | U.S.S.R. | 73/84 |
| 568333 | 3/1945 | United Kingdom | 73/84 |

*Primary Examiner*—Hezron E. Williams
*Assistant Examiner*—Daniel S. Larkin
*Attorney, Agent, or Firm*—Henry S. Miller; Rhodes & Ascolillo

[57] ABSTRACT

A gauge for measuring the relative resiliency of golf greens including a barrel shaped device with a base having foot pads to hold the instrument on the green and a calibrated spring to drive a measuring tip into the turf and a scale indicator attached to the barrel for providing the information indicative of the condition of the green.

4 Claims, 3 Drawing Sheets

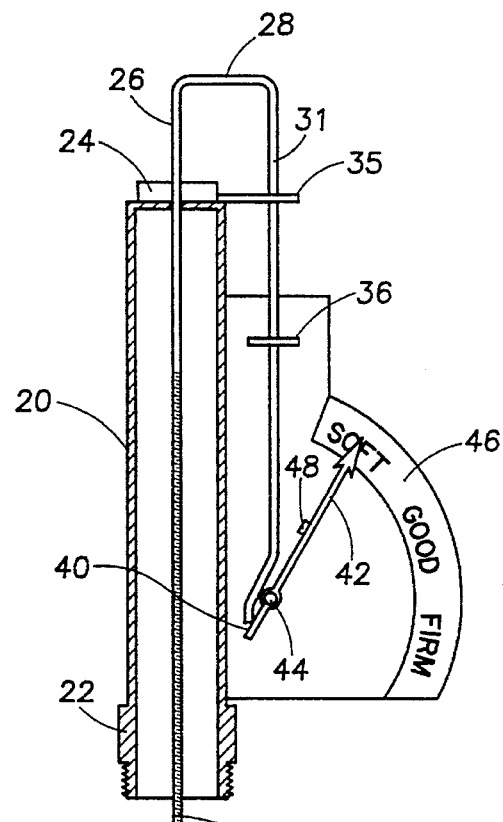
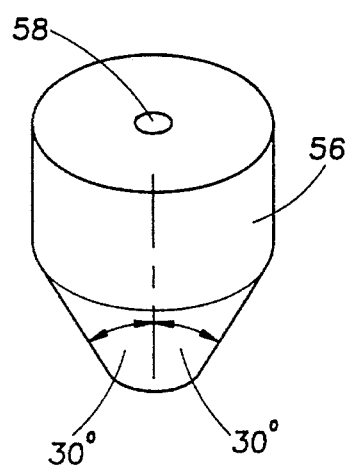
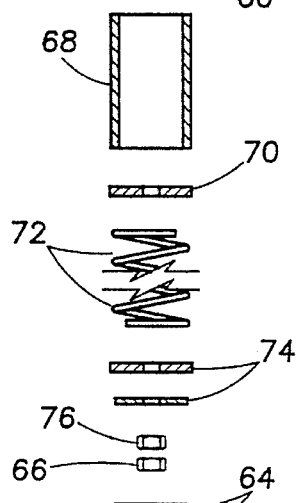
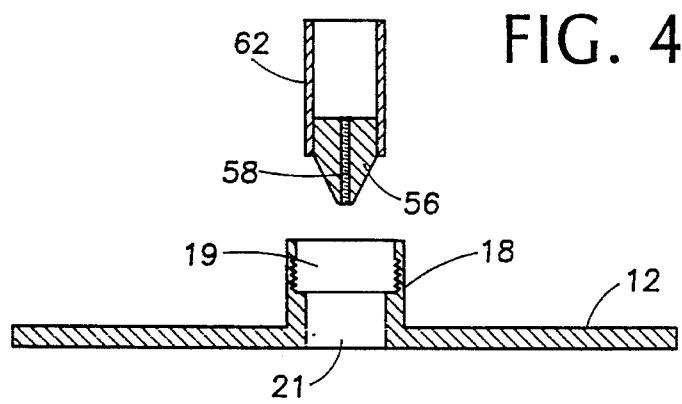
FIG. 5
FIG. 4

INSTRUMENT FOR MEASURING THE RELATIVE RESILIENCY OF GOLF GREENS

BACKGROUND OF THE INVENTION

1. Field of the Invention

This invention relates generally to a testing apparatus and more particularly to an apparatus for testing the relative resiliency of golf greens.

2. Description of the Prior Art

Perhaps the most sophisticated form of agrarian art is seen in the golf course green keeper. At least an artist, the skill in keeping a golf green in goes far beyond simply cutting the grass on a regular basis. The goal of the greens keeper is not only to have a well groomed green but to have eighteen well groomed greens that will have consistent factors for the golfer as he or she plays a round. Part of the difficulty in maintaining a green is the weather and the location of the green. Factors that will cause some greens to dry out faster than others include wind and the exposure to sun. The most difficult situation for the greens keeper is the green that, because of size, shape or placement, one green will have several variables that will effect the golf ball as it rolls toward the cup. For example, the green could have a low area that collects moisture and a high area that drains quickly and is prone to drying out. If the greens keeper waters the green equally the result is obvious.

Instruments have been suggested to determine the hardness of soil, however such devices are generally used to obtain scientific data for farmers or civil engineering applications. Hardness of the underlying soil has little to do with turf resiliency. Known devices are pointed and penetrate several inches into the soil, far deeper than is needed to measure the hardness of a golf green. The deep measurements are in fact less accurate for the greens keeper purposes than a shallow measurement that will produce results that most likely effect the performance of a rolling golf ball. Currently, at known golf courses the green condition is measured by inserting a golf tee into the green and an opinion formed by the one measuring, which is then debated by, and subject to review by the greens committee of the particular Club.

U.S. Patents of which Applicant is aware that relate to measuring and testing hardness include, U.S. Pat. No. 4,061,021 issued Dec. 6, 1977 to Baldwin et al. for a recording soil penetrometer which uses a spike like probe to determine and record the mechanical properties of the soil. U.S. Pat. No. 4,136,554 issued Jan. 30, 1979 to Larson discloses a tester for inflated items that includes a dial indicator and a plunger having a hemispherical end that engages the test piece. U.S. Pat. No. 4,302,967 issued Dec. 1, 1981 to Dufey shows an apparatus for measuring the mechanical characteristics of soil, which also uses a sharp pointed probe. U.S. Pat. No. 5,291,774 issued Mar. 8, 1994 discloses a ball testing apparatus that include indicia and a needle for indicating, on the indicia, the condition of the ball.

The most interesting U.S. Patent is U.S. Pat. No. 4,887,457 issued Dec. 19, 1989 to Thomas for measuring gauge for determining the hardness of a golf green. The instrument includes a housing and a spring biased probe extending from one end of the housing and a scale, connected to the probe extending from the opposed end. In use, the housing is placed on the green and pressed against the green by handles on the housing. The elongated, tapered probe with its pointed tip will be forced into the green against the spring bias dependent upon the soil condition. As the probe recedes into the housing the scale extends from the housing and is secured by one of the handles which rotate and locks the scale in place. The instrument is removed and the scale read and compared to other readings. The instrument is similar to the other prior art in that it if fact measures the mechanical characteristics of the soil using a sharp pointed probe and does not provide a reading that is indicative of conditions that will actually effect the roll of a golf ball across the surface being tested.

SUMMARY OF THE INVENTION

The invention is directed to an instrument which will quickly and efficiently register the resilience of a golf green surface. The resilience of a golf green has a great deal of effect on the roll of the golf ball as it lands on the green. In common practice the golfer will chip onto the green, giving the ball a high loft and back spin. The proper resiliency of the green will cause the ball to stop when it lands, in some cases the ball will roll back in the direction of the player. If the green is not properly groomed, it could lack resiliency and the ball will bounce and roll on away from the player and probably the cup. A green that is too soft will be difficult to putt and make the roll of the ball uncertain. These factors involve the length and condition of the grass and the matt under the grass. The soil below the matt is a negligible factor in the ball roll equation except for a very thin surface layer immediately below the matt.

The invention consists of a barrel shaped instrument, having a base which includes a pair of opposed extensions that are used to stand on and hold the instrument on the green. An adapter on the base allows the barrel to be threaded into the base and forms the fundamental structure of the instrument. The adapter contains an aperture that includes the base and is utilized for the projection of the instrument measuring tip. The distal end of the barrel is sealed except for a centrally located aperture which allows a "U" shaped control rod to pass through. One leg of the control rod projects down through the aperture and the contents of the barrel which include, a spacer, a compression spring, washers and lock nuts, another spacer and finally terminates threadedly engaging the measuring tip. The other leg of the control rod extends down the outside of the barrel where the end comes in contact with and operates an arrow that pivots and displays the instrument reading over a calibrated panel.

In operation the instrument is placed on the green and the measuring tip is raised against the bias of the spring by lifting the base of the control rod. A locking latch on the outside of the barrel engages a detent in the control rod and locks the control rod in place. The user stands on the base extensions and releases the locking latch. The spring drives the measuring tip down into the grass and the matt below it and may make a dent in the surface of the soil. The extent of the movement is displayed by the arrow which was moved by the external arm of the control rod. A small shoe brake connected to the arrow holds the arrow in position whereby the instrument may be removed from the green and examined. The arrow is simply returned to the original position by a light finger force prior to the next measurement.

It is therefore an object of the invention to provide a new and improved instrument for measuring the resiliency of a golf green.

It is another object of the invention to provide a new and improved instrument for measuring resiliency that is compact, light in weight and easy to operate.

It is a further object of the invention to provide a new and improved instrument for measuring resiliency that uses readily available parts.

It is still another object of the invention to provide a new and improved instrument for measuring resiliency that is low in cost.

It is still a further object of the invention to provide a new and improved instrument for measuring resiliency which may be easily and efficiently manufactured and marketed.

It is another object of the invention to provide a new and improved instrument for measuring resiliency which is of a durable and reliable construction.

These, together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is an exploded view of the invention detailing the particular parts.

FIG. 5 is an enlarged side elevation view of the measuring tip of the invention.

DETAILED DESCRIPTION OF A PREFERRED EMBODIMENT OF THE INVENTION

Figure 1:
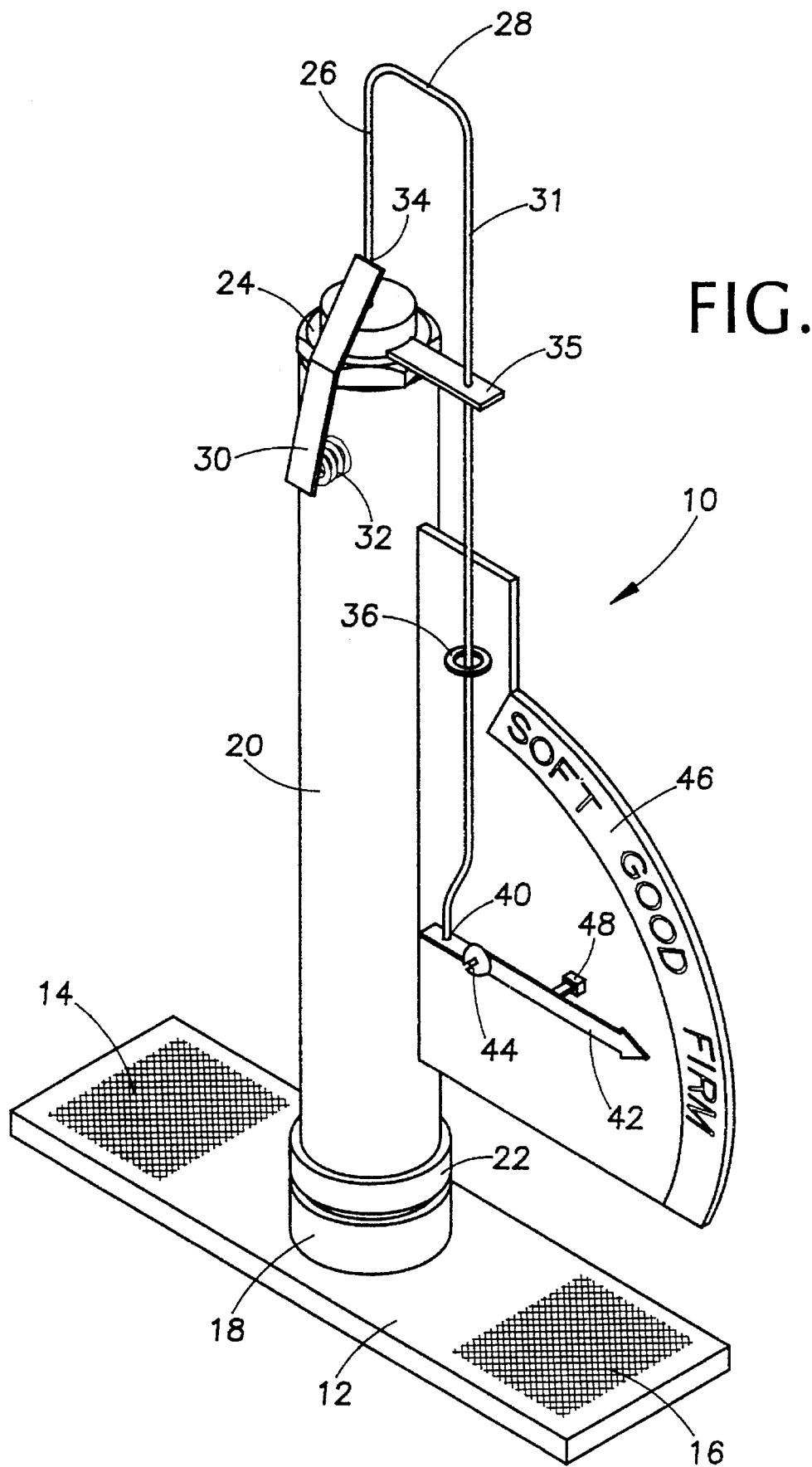
FIG. 1 is a perspective view of the invention.

Referring now to FIG. 1, the invention is shown generally at 10. The base member 12 includes two extensions 14,16 for use as foot pads to hold the instrument on the green during a test. An adapter 18 is affixed to the base as by welding and contains an aperture 19 that aligns with an aperture 21 of similar size in the base. A barrel 20 engages the adapter 18 through coupler 22. The distal end of the barrel contains a plug 24 with an central aperture allowing leg 26 of "U" shaped control rod 28 to extend into the interior of the barrel. A releasable locking latch 30 is biased by spring 32 and pivots against leg 26 which contains a detent 34 for locking the instrument in a "ready" position immediately prior to performing a test. Leg 26 of the control rod passes down the outside of barrel 20 through guides 35 and 36 to a point where the end tip 40 engages the end of arrow 42 which pivots about pin 44. As the control rod moves down, the arrow will pivot upward and indicate on the panel 46 the condition of the turf, soft, good or firm. A small metal friction shoe 48 attached to the arrow rides on panel 46 and holds the arrow in place after the test to allow the user to pick the instrument up and examine the reading. Light finger pressure on the arrow will return it to the start position.

Figure 2:
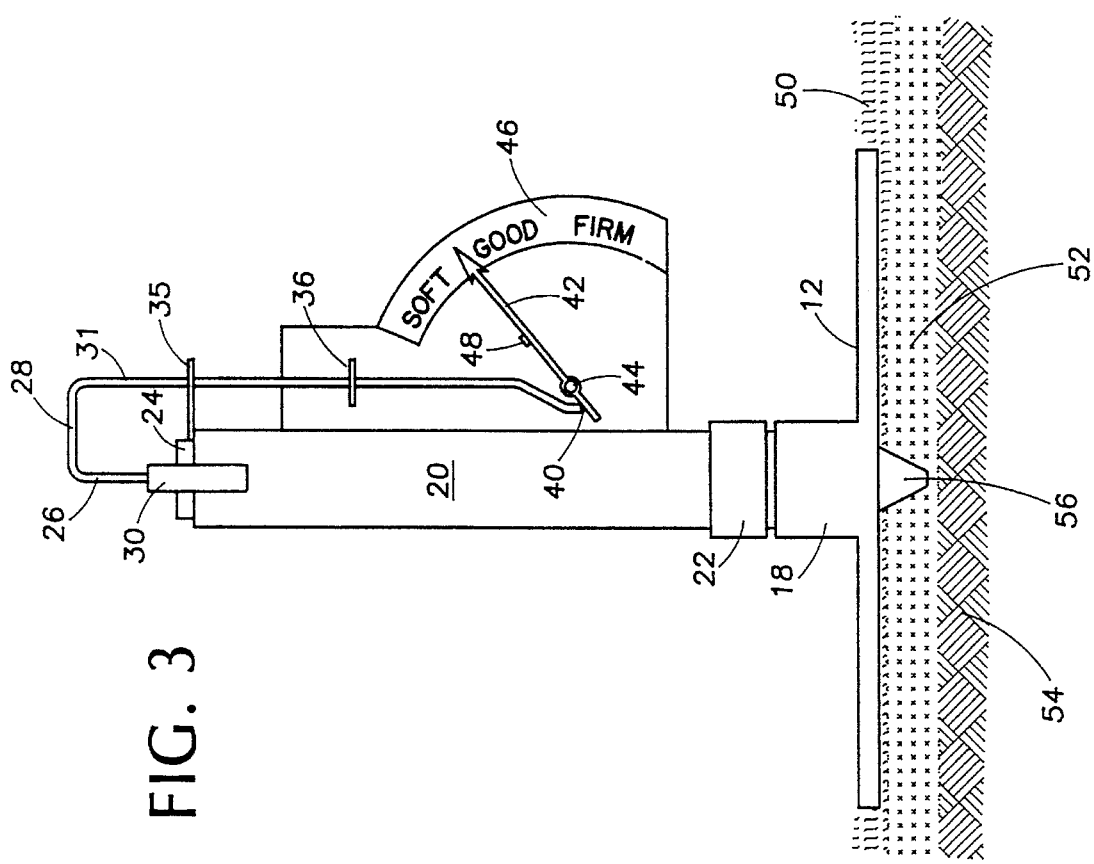
FIG. 2 is a side elevation view of the invention shown on hard turf.
Figure 3:
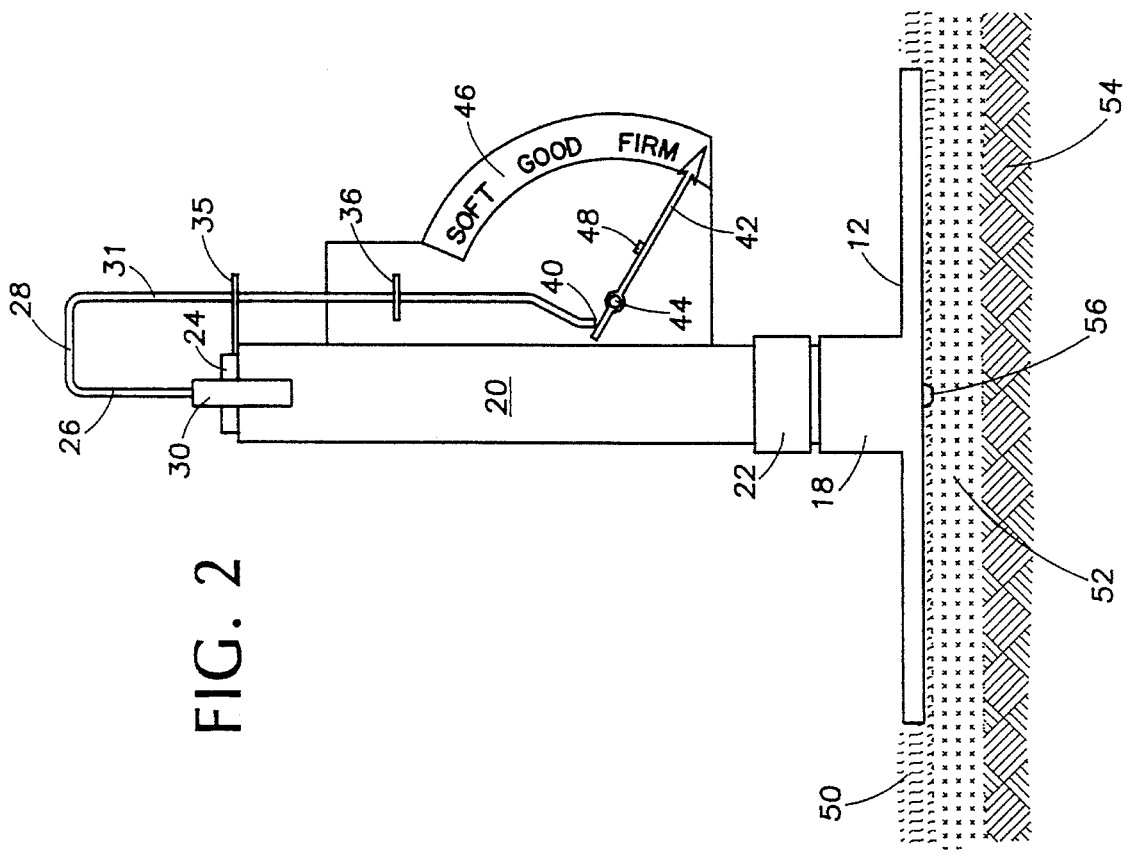
FIG. 3 is a side elevation view of the invention shown on soft turf.

Concerning FIGS. 2 and 3, base 12 of the invention is placed on the turf of the golf green which consists generally of bent grass 50 mowed to a height of approximately 5/32 of one inch and a matting 52 ranging in thickness from ¼ to ⅜ of one inch. Below the matt is soil 54. A test is performed by raising the "U" shaped control rod 28 until the locking latch engages the detent on arm 26 as shown in FIG. 2. The lock is released and a spring bias will apply a calibrated force to the measuring tip 56 which will move into the turf and make a dent in the surface including, under certain wet circumstances the soil below the turf. Arm 31 will move down and cause the arrow to rise according to the distance that the measuring tip moves into the turf. Shoe brake 48 holds the arrow in place until reset by the user.

Internal components of the instrument are shown in FIG. 4. The measuring tip 56 contains internal threads 58 adapted to engage threads 60 on the control arm 26. A spacer 62 surrounds the measuring tip and acts as a guide for the tip within the barrel 20. Washers 64 and nut 66 secure the measuring tip to the rod 26. A second spacer 68 with washer 70 provide a stop for one end of compression spring 72. Washers 74 and nut 76 threaded on arm 26 provide the stop for the other end of spring 72. When the control rod 28 is raised, washers 74 cause the spring 72 to compress against the spacer 68 and provide the driving force for the measuring tip 56. The nut 76 provides calibration adjustment for the spring force of the instrument.

In FIG. 5 the measuring tip 56 is shown and is cylindrical in length and frustro-conical at the end with the slope of the cone surface 30 degrees to the longitudinal axis represented by threaded aperture 58. The end 78 of the cone is flat and approximately ½ inch in diameter.

It should be understood, of course, that the foregoing disclosure relates to only a preferred embodiment of the invention and that numerous modifications of alterations may be made therein without departing from the spirit and scope of the invention as set forth in the appended claims.

What is claimed is:

1. A gauge for measuring the relative resilience of a golf green turf comprising:

a flat base having a bore extending therethrough;

the base includes foot lads for receiving a users feet and stabilizing the base;

a barrel shaped housing, mounted transverse to and threadingly engaging the base, coincident with the bore on one end and having a cap on another end;

a probe assembly, axially translatable within the barrel for movement between a retracted position and an extended position, said assembly including a measuring tip extendable through the bore for abutment with the golf green turf;

a spring within the barrel for selectively biasing the probe assembly into the extended position under a predetermined force;

a scale means with indicia and a pivoting arrow for indication resilience of the turf, affixed to the barrel, and means cooperating with the measuring tip for translating movement of the measuring tip into movement of the arrow;

means for moving the probe assembly against the bias of the spring from the extended position to the retracted position within the barrel;

a releasable locking means for holding the probe assembly in the retracted position;

the means for translating movement of the measuring tip includes a "U" shaped control rod means threadedly engaging the measuring tip, with one arm extending longitudinally through the barrel cap and then transversely to the said longitudinal axis, and externally parallel to the barrel, terminating in contact with said arrow.

2. A gauge for measuring relative resiliency according to claim 1 further including: a friction brake attached to the arrow for restraining the arrow from movement cause by the force of gravity.

3. A gauge for measuring relative resiliency according to claim 2 wherein: the measuring tip is frusto-conical in shape.

4. A gauge for measuring relative resiliency according to claim 3 wherein: the probe assembly includes, a measuring tip, a first spacer sleeve attached to the measuring tip, a compression spring for biasing the measuring tip, a second spacer sleeve for separating the spring from the barrel cap, and a threaded nut means for engaging the control rod for adjusting the retracted spring bias and calibrating the instrument.

* * * * *